(12) United States Patent
Van Lierde et al.

(10) Patent No.: US 10,346,504 B2
(45) Date of Patent: Jul. 9, 2019

(54) 3D MODELLING OF BODIES

(71) Applicant: DENTSPLY IMPLANTS NV, Hasselt (BE)

(72) Inventors: Carl Van Lierde, Meerbeke (BE);
Joris Vanbiervliet, Kessel-Lo (BE);
Pieter De Ceuninck, Gelrode (BE);
Stefaan Dhondt, Webbekom (BE);
Veerle Pattijn, Kessel-Lo (BE); Jan Heyninck, Mechelen (BE)

(73) Assignee: DENTSPLY IMPLANTS NV, Hasselt (BE)

( * ) Notice: Subject to any disclaimer, the term of this patent is extended or adjusted under 35 U.S.C. 154(b) by 513 days.

(21) Appl. No.: 14/428,201

(22) PCT Filed: Sep. 17, 2013

(86) PCT No.: PCT/EP2013/069230
§ 371 (c)(1),
(2) Date: Mar. 13, 2015

(87) PCT Pub. No.: WO2014/041186
PCT Pub. Date: Mar. 20, 2014

(65) Prior Publication Data
US 2015/0248538 A1    Sep. 3, 2015

(30) Foreign Application Priority Data

Sep. 17, 2012    (GB) .................................... 1216537.9

(51) Int. Cl.
*G06F 17/00*    (2019.01)
*G06F 17/10*    (2006.01)
(Continued)

(52) U.S. Cl.
CPC ............ *G06F 17/10* (2013.01); *G06T 17/005* (2013.01); *G16H 50/50* (2018.01)

(58) Field of Classification Search
USPC .................................................. 345/428, 419
See application file for complete search history.

(56) References Cited

U.S. PATENT DOCUMENTS

| | | | | |
|---|---|---|---|---|
| 7,352,369 B2* | 4/2008 | Spicer | ..................... | G06T 17/30 345/419 |
| 8,081,180 B2* | 12/2011 | Storti | ..................... | G06T 17/00 345/420 |

(Continued)

FOREIGN PATENT DOCUMENTS

| | | |
|---|---|---|
| JP | H05-506730 A | 9/1993 |
| JP | 2002-528832 A | 9/2002 |

(Continued)

OTHER PUBLICATIONS

International Search Report (ISR) dated Dec. 11, 2013, for PCT/EP2013/069230.

(Continued)

*Primary Examiner* — Kimbinh T Nguyen
(74) *Attorney, Agent, or Firm* — Bacon & Thomas, PLLC

(57) ABSTRACT

System or components such as software for 3D modelling of bodies is described. This can be realized by a computer based method for modelling a body by scanning a determined space divided into elementary spaces, each elementary space being assigned a signed distance parameter indicative of the distance of said elementary space to said body and a weight parameter indicative of the importance of the distance parameter; said scanning of said body providing scanned points and each scanned point thus obtained possibly modifying said signed distance and weight parameters of each elementary space of said determined space; wherein, each one of selected elementary spaces is modified by subdividing said selected elementary space into higher level elementary spaces defined by the same parameters; wherein, in order to decrease details of the model of said body, said (Continued)

elementary spaces are modified by replacing selected elementary spaces with lower level elementary spaces.

23 Claims, 8 Drawing Sheets

(51) Int. Cl.
*G06T 17/00* (2006.01)
*G16H 50/50* (2018.01)

(56) References Cited

U.S. PATENT DOCUMENTS

| | | | | |
|---|---|---|---|---|
| 8,160,351 | B2* | 4/2012 | Sandstrom | G01N 21/956 356/237.4 |
| 8,660,353 | B2* | 2/2014 | Storti | G06K 9/342 345/419 |
| 2002/0130854 | A1* | 9/2002 | Perry | G06T 15/00 345/420 |
| 2002/0149582 | A1 | 10/2002 | Pope et al. | |
| 2003/0197698 | A1 | 10/2003 | Perry et al. | |
| 2009/0202155 | A1 | 8/2009 | Hayashi et al. | |
| 2010/0085357 | A1 | 4/2010 | Sullivan et al. | |
| 2010/0231583 | A1* | 9/2010 | Furukawa | G01B 11/24 345/419 |
| 2012/0287129 | A1* | 11/2012 | Storti | G06K 9/342 345/424 |
| 2013/0335417 | A1* | 12/2013 | McQueston | A61B 6/145 345/424 |

FOREIGN PATENT DOCUMENTS

| | | |
|---|---|---|
| JP | 2003-006672 A | 1/2003 |
| JP | 2012-505445 A | 3/2012 |
| WO | 9116700 A1 | 10/1991 |
| WO | 0025896 A1 | 5/2000 |
| WO | 2009/133131 A1 | 11/2009 |

OTHER PUBLICATIONS

Written Opinion dated Dec. 11, 2013, for PCT/EP2013/069230.
British Search Report dated Mar. 7, 2013, for GB 1216537.9.
International Preliminary Report on Patentability (IPRP) dated Feb. 3, 2015, for PCT/EP2013/069230.
Second Written Opinion dated Nov. 18, 2014, for PCT/EP2013/069230.
Lorensen, W. E.; Cline, Harvey E. (1987). "Marching cubes: A high resolution 3d surface construction algorithm". ACM Computer Graphics vol. 21 (4) pp. 163-169.
Akio Doi and Akoi Koide, "An efficient method of triangulating equi-valued surfaces by using tetrahedral cells", IEICE Trans Commun. Elec. Inf. Syst, E-74(1) pp. 213-224, 1991.
Chen, Yang; Gerard Medioni (1991). "Object modelling by registration of multiple range images". Image Vision Comput. (Newton, MA, USA: Butterworth-Heinemann) pp. 145-155.
Fuhrmann, Simon, Darmstadt Tu, Goesele Michael, "Fusion of depth maps with multiple scales", www.gris.informatik.tu-darmstadt.de, vol. 30, No. 6, pp. 1-8, Dec. 1, 2011.
Izadi, S. et al., "KinectFusion: Real-time 3D reconstruction and interaction using a moving depth camera", research.micorsoft.com, pp. 1-10, Oct. 16, 2011.
Frisken S. F. et al., "Adaptively sampled distance fields: A general representation of shape for computer graphics", Computer Graphics, Siggraph 2000 Conference Proceedings, New Orleans, LA, Jul. 23-28, 2000, New York, NY, US, pp. 249-254, Jul. 23, 2000.
B Curless, "A volumetric method for building complex models from range images", published 1996, Stanford University, available from http://graphics.stanford.edu/papers/volrange/volrange.pdf.
R Sagawa, "Robust and adaptive integration of multiple range images with photometric attributes", published 2002, University of Tokyo, available from http://www.am.sanken.osaka-u.ac.jp/~sagawa/pdf/cvpr01.pdf.
Japanese Office Action dated Jun. 20, 2017, for JP 2015-531597, and English translation thereof.

* cited by examiner

3D MODELLING OF BODIES

The current invention relates to a method, system and components such as software for 3D modelling of bodies, especially for use in dentistry and modelling of dentitions, jaws, tooth setups etc.

BACKGROUND OF THE INVENTION 3D digitization of human bodies, human body parts, mechanical object and thus bodies in general is widely adopted and applied nowadays. During this digitization process, the body is scanned by a scanning device in all three dimensions in order to obtain measurement data or scanned points about the body. Then, the scanned points are further processed and a digital representation is obtained modelling the body in a format suitable for storage and processing on a computer system. This digital representation can then be further used for digital manipulations like volume rendering to obtain an image of the scanned object for visualization on a display. The representation can also be further processed using CAD/CAM technology. The whole process of scanning a body and obtaining a digital representation is generally referred to as the 3D scanning pipeline. Some scanners that are available, for example intra-oral scanners used for the digitization of patient's dentition, can parallelize some steps in this pipeline obtaining a digital representation of the dentition. This allows an incremental scanning approach where basically the digital representation and thus also the visualization on the display is growing or extending while more data measurements are captured. Using this kind of scanners, the user of the scanner gets a visual image of the digitized body on his display while the scanning is still in process. The user thus doesn't have to wait for the scanner to complete first all the measurements before having a first digital representation. A significant limitation however of the scanning pipeline in this type of scanners is that they cannot incrementally increase the level of detail in the digital representation, i.e. the resolution of the surface they model cannot incrementally grow in areas where more measurements are being made.

One step that is common in the 3D scanning pipeline is the acquisition or scanning step where data about the body is captured or measured and all measurements are converted to scanned points in order to represent all measurements in a global coordinate system, i.e. irrespective of the different scanner positions that were for example used. This acquisition or capturing of data is typically done by a scanning device, i.e. the actual scanner. For the scanning itself, different scanning equipment exists such as Computed Tomography (CT) scanners (e.g. CBCT, conventional medical CT, $\mu$CT . . . ), optical scanners, mechanical i.e. tactile scanners, MRI scanners, ultrasound scanners and the like. Depending on the type of scanner all types of measurement data can be collected such as discrete distance measurements, surface geometry, colour and texture. Typically, the scanning process is done in several steps in time or in space where several scanned images comprising the measurement data are obtained from different viewpoints. Therefore, different sets of measurements can be defined in different coordinate systems, depending on the position of the scanner. This data is then further processed during the acquisition step to construct a digital point-cloud representation of the scanned body. In other words, all the sets of measurements that are defined in different coordinate systems are transformed to a single global coordinate system. This way, all measurement data of the body is represented in a single three dimensional coordinate system. The point cloud representation already inherently constitutes a method to visualize the measurements. It suffices to display all the points in their coordinate system on a display to have an impression of the scanned body. However, this point cloud representation is not always suited to provide the user with an easy to recognize and/or interpret digital, three-dimensional image of the body. The point cloud is generally not considered as a digital representation, but as an intermediate point to obtain one.

Therefore, in a second surface reconstruction step, the point cloud representation is typically converted into a digital surface representation for rendering on a display. The conversion step from a point cloud to a surface representation usually comprises a meshing operation during which the surface is reconstructed as a surface mesh based on the point cloud. One commonly used type of surface mesh is a triangular mesh in which the surface representation is made of different triangles.

In the prior art article from Curless and Levoy, *A volumetric method for building complex models from range images* (Proceeding SIGGRAPH '96 Proceedings of the 23$^{rd}$ annual conference on Computer graphics and interactive techniques), different surface reconstruction techniques are outlined that convert a point cloud into such a (triangular) surface mesh. They subdivide the surface reconstruction techniques mainly in two groups, non-volumetric and volumetric techniques. The non-volumetric techniques have the disadvantage that they are very time-consuming and do not always result in a correct surface mesh exhibiting intersecting or overlapping triangles. Moreover, these surface reconstruction techniques do not work well in case of noisy input data. Volumetric surface reconstruction techniques on the other hand, always result in correct surface meshes. One type of volumetric surface reconstruction techniques described uses the fitting of implicit functions for the generation of the surface mesh. This technique can work with different degrees of detail or thus resolution throughout the surface. However, it has the disadvantage that all processing steps starting from the point cloud must be completely redone when such a change in detail is desired or when new measurement data is acquired and added to the point cloud. This non-incremental approach limits their usability.

Another type of volumetric surface reconstruction techniques compatible with incremental scanning approaches is based on a grid approach. They typically make use of range images as measurement data, i.e. distance measurements on a regular sampling lattice, as input, which are captured incrementally. They also have the advantage that they are fast and that they can handle noisy input data. Their main disadvantage is that these cannot handle different levels of detail in different parts of the surface representation.

SUMMARY OF THE INVENTION

It is the object of the present invention to provide an alternative method, system or components such as software for 3D modelling of bodies.

Embodiments of the present invention can obviate at least one of the prior art disadvantages and, thus, provide an improved method, system and components such as software to model a body by scanning. Each scanning step provides a set of points representing the body or part of the body in space. And these points are further used by the method to construct and refine this model. Computed Tomography (CT) scanners (e.g. CBCT, conventional medical CT, $\mu$CT .

. . ), optical scanners, mechanical i.e. tactile scanners, MRI scanners, ultrasound scanners and the like can be used with any of the methods or systems of the present invention.

According to a first aspect of the invention this is realized by a computer based method for modelling a body by scanning a determined space divided into elementary spaces, each elementary space being assigned a signed distance parameter indicative of the distance of said elementary space to said body and a weight parameter indicative of the importance of the distance parameter; said scanning of said body providing scanned points and each scanned point thus obtained possibly modifying said signed distance and weight parameters of each elementary space of said determined space; wherein, in order to increase details of the model of said body, each one of selected elementary spaces of said determined space is modified by subdividing said selected elementary space into higher level elementary spaces defined by the same parameters as said selected elementary spaces; wherein, in order to decrease details of the model of said body, said elementary spaces of said determined space are modified by replacing selected elementary spaces with lower level elementary spaces defined by the same parameters as said selected elementary spaces.

In said subdividing, said higher level elementary spaces together occupy the same space as said selected elementary space. Said higher level elementary spaces do not necessarily replace said selected elementary space but can exist together in said determined space. Said higher level elementary spaces are also elementary spaces and thus possibly modified by each scanned point provided by said scanning.

In said replacing said selected elementary spaces with said lower level elementary spaces, said lower level elementary spaces together occupy the same space as said selected elementary spaces. The total amount of said lower level elementary spaces is smaller than the total amount of said selected elementary space. Said lower level elementary spaces are also elementary spaces and thus possibly modified by each scanned point provided by said scanning. The method according to embodiments of the present invention can be used for the digitization of a dental arch.

Embodiments of the present invention provide a computer based system for modelling a body from a scanning of a body in a determined space, the said scanning of said body providing scanned points, the system including a processor adapted to divide the determined space into elementary spaces, the processor also being adapted for assigning for each elementary space a signed distance parameter indicative of the distance of said elementary space to said body and a weight parameter indicative of the importance of the distance parameter; and each scanned point optionally modifying said signed distance and weight parameters of each elementary space of said determined space; wherein, in order to increase details of the model of said body, the processor is adapted to modify each one of selected elementary spaces of said determined space by subdividing said selected elementary space into higher level elementary spaces defined by the same parameters as said selected elementary spaces; wherein, in order to decrease details of the model of said body, the processor is adapted to modify said elementary spaces of said determined space by replacing selected elementary spaces with lower level elementary spaces defined by the same parameters as said selected elementary spaces.

In said subdividing, said higher level elementary spaces together occupy the same space as said selected elementary space. Said higher level elementary spaces do not necessarily replace said selected elementary space but can exist together in said determined space. Said higher level elementary spaces are also elementary spaces and thus possibly modified by each scanned point provided by said scanning.

In said replacing said selected elementary spaces with said lower level elementary spaces, said lower level elementary spaces together occupy the same space as said selected elementary spaces. The total amount of said lower level elementary spaces is smaller than the total amount of said selected elementary space. Said lower level elementary spaces are also elementary spaces and thus possibly modified by each scanned point provided by said scanning.

A second aspect of the present invention is realized by using the above method or system to obtain a digital volume or surface representation of a body.

An advantage of embodiments of the present invention is that the model of the body obtained is incrementally refined by every scanning step and thus by every addition of scanned points without having to reprocess the already scanned points.

A further advantage of embodiments of the invention is that the local level of detail of the model obtained can be changed at any time during the scanning without having to reprocess the already scanned points.

A further advantage of embodiments of the invention is that a digital volume or surface representation can be obtained from the model obtained at any time during the scanning process in shorter processing time than when the digital representation is obtained directly from the scanned points.

BRIEF DESCRIPTION OF THE DRAWINGS

The invention shall be better understood in light of the following description and of the accompanying drawings were

DETAILED DESCRIPTION OF THE INVENTION

Definitions

Figure 1:
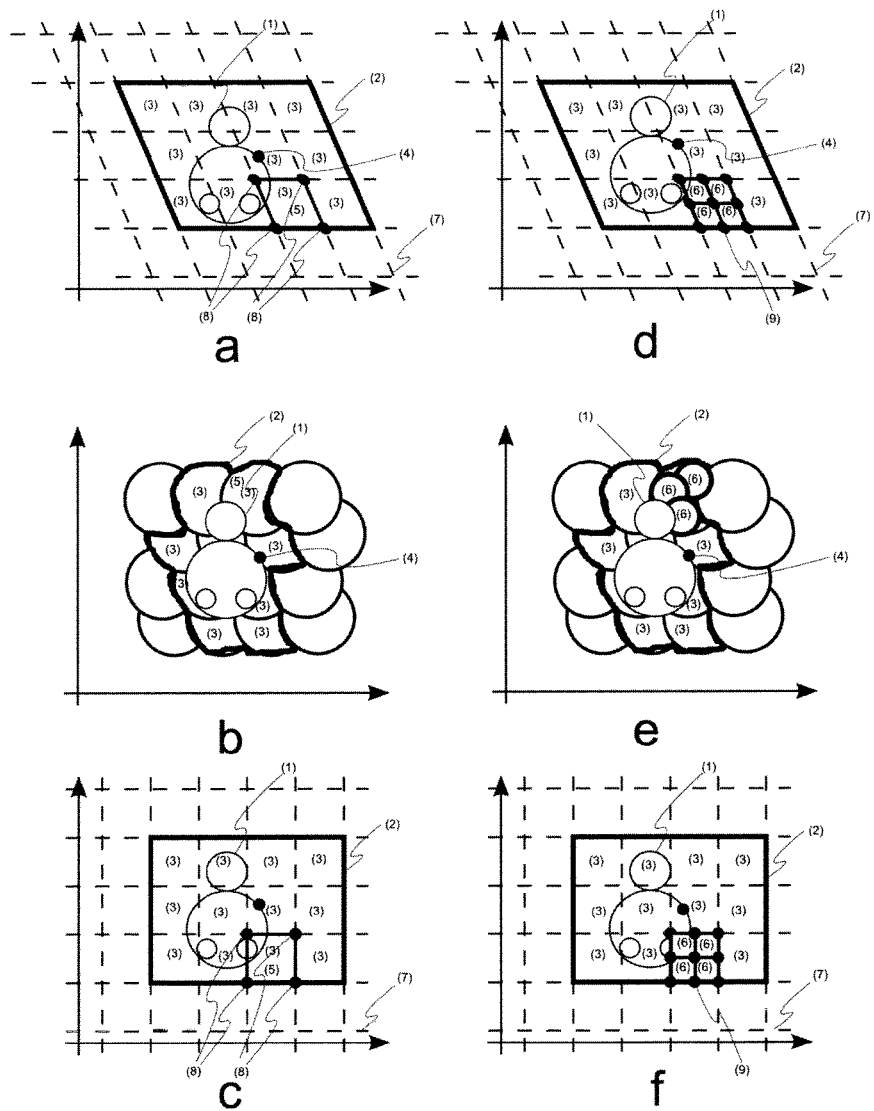
FIG. 1 shows an illustrative example of a determined space comprising elementary spaces according to preferred embodiments of the present invention.

The following terms are provided solely to aid in the understanding of the invention.

The term "body", as used in disclosing the present invention, refers to a part of or a complete human body, animal body or physical object in general.

The term "determined space" is used throughout the description and claims to define a three dimensional volume relative to a body indicating the spatial boundaries within which further methods, algorithms, processing or modelling apply.

The term "digital representation", as used in disclosing the present invention, refers to the digital format comprising volume and surface information of a body that was digitized, i.e. a digital model of the volume or surface of the body. This information thus outlines the volume and surface of the digitized body in the determined space with a certain precision. This digital representation can then further be used for visualization of the body on a display by for example volume rendering, i.e. the generation of an image from the digital volume representation. The digital representation can also be further used for further processing. For example, the digital representation of a human hip bone could be used to make a hip prosthesis. The digital representation is also optimized for storage and processing on a computer system. A typical popular digital representation format is a triangle mesh. In a triangle mesh, the body is modelled as a set of triangles in three dimensions that are connected by their common edges or corners. Various methods exist to operate on and store such a triangle mesh. For example a surface rendering method can be applied to such a triangle mesh to visualize it on a display as a wireframe or a smoothly shaded surface.

The term "octree", as used in disclosing the present invention, refers to a hierarchical decomposition of 3D-space along its component axes. The octree is thus used as a representation of a three dimensional determined space where each node in an octree represents some elementary space. Each node can have eight children representing the division of an elementary space in eight smaller spaces each represented by a child node. Every child node can, on its turn, again have child nodes and so on. A conventional octree guarantees regular, non-overlapping node spacing, thus is well-suited as a container for rectilinear scalar field data. How this hierarchical container is used, however, varies with the application. The present invention uses a particular way of constructing the octree in one of the embodiments.

The term "scanning", as used in disclosing the present invention, is the process to obtain scanned points uniquely defined in space providing information about the body that is being scanned. To define the point in space the point can for example be represented by coordinates in any suitable reference system such as a global reference system. But the point can also comprise more information, for example any or all of colour information, texture information, whether the point is outside or inside the body. The scanning can be done in different steps in time, resulting in one of more points during every scanning step. To obtain those points the scanning process typically involves a few steps. In one example, distance measurements are performed from the tip of a scanner to the surface of the body to be scanned either directly or indirectly, by means of a scanning device. This scanning device can use different techniques for obtaining these distance measurements, e.g. time-of-flight measurement of a light pulse, a phase shift method, an ultrasonic time-of-flight method, a frequency modulation method, interferometric techniques . . . . Some scanning devices may also provide additional measurement data such as a confidence value related to the accuracy of the measurement or a colour measure, or information on the position of the scanning device, or any other type of information that can be captured with the scanning device or calculated from input captured by the scanning device such as a normal vector. The distance measurements obtained by the scanning device may then be converted by a processing unit into 3D points in a local coordinate system that can for instance be associated with the tip of the scanner. These 3D points can then be transformed to a global coordinate system using for example a registration algorithm. Additional measurement data can also be used to determine this transformation. These 3D points would then be the points referred to by the present invention. The present invention is not limited to this way of obtaining measurement data, any acquisition method can be used as long as points in a determined space are available to the method. Typical scanning methods and apparatus that can be used with the present invention are MRI, Computed Tomography (CT) scanners (e.g. CBCT, conventional medical CT, μCT . . . ), optical scanners, mechanical i.e. tactile scanners, MRI scanners, ultrasound scanners and the like.

The term "regular sampling units" relates to equally sized sampling units. These equally sized sampling units are not necessarily cube shaped for example, because they could also be rectangular.

Particular Ways of Carrying Out the Method According to the First Aspect of the Invention In a particular a method 100 of carrying out the first aspect of the invention is described with reference to FIG. 6 whereby a scanning of the body provides different scanned points (4). All scanned data is loaded into a computer in step 101—such as computer 54 of FIG. 5. Computer 54 is adapted to carry out any of the methods of the present invention. A determined space (2) is divided into elementary spaces (3) in step 102 as illustrated in FIGS. 1-*a*, 1-*b* and 1-*c*. As the model of the body (1) that will be obtained by the method is using these elementary spaces (3), only the part of the body within this determined space will be modelled. For clarity, the FIGS. 1-*a*, 1-*b* and 1-*c* use a two dimensional representation, but the invention is not limited thereto. Each of these elementary spaces (3) has a signed distance parameter and a weight parameter assigned to it in step 103. The signed distance parameter is indicative of the distance between the elementary space (3) it is assigned to and the body (1) that is to be modelled from the scanning of the body. The weight parameter is indicative of the importance of this distance parameter. For example, when the model would be used later on to create a digital surface representation of the body, such as a triangle mesh, the weight value indicates how much importance can be given to its accompanying signed distance value. From the scanning of the body different scanned points (4) are obtained. Said scanned point uniquely defines a point within the determined space, for example by being given the coordinates within a global reference system. The assignment of variables to a scanned point can also comprise implicitly or explicitly information to determine whether the point is inside, outside or on the surface of the body. This type of information is typically provided by the scanning device. The ways in which these scanned points are acquired by the scanning are not limiting on the present invention. In step 104, for each scanned point that is then obtained by the scanning of the body, the signed distance and weight parameter of each elementary space is optionally modified taking into account the newly scanned point as this point comprises information on the distance from the elementary spaces to the body. In order to increase the detail of the model of the body in step 105, selected elementary spaces (5) are modified by subdividing these selected elementary spaces into smaller elementary spaces (6) that have also a signed distance and weight parameter assigned. The selected elementary spaces (5) are considered to be lower level elementary spaces relative to the smaller elementary spaces (6) that are considered higher level elementary spaces. The detail of the model is hence improved in the location where the elementary spaces (5) are divided into smaller elementary spaces (6) resulting in a locally improved detail of the model. This process of increasing the detail of the model can be performed at any time during the modelling of the body. The smaller elementary spaces are then also elementary spaces that can possibly be modified when new points are provided by scanning. The dividing of an elementary space (5) does not mean that this elementary space ceases to exist. In this case, the smaller elementary spaces (6) can thus be seen as higher level elementary spaces relative to the elementary space (5) they originated from, the lower level elementary space. Again, when a new point is added to the model, the signed distance and weight parameter of both this original elementary space and smaller elementary spaces can possibly be modified. As with the increasing of the details of the model, one can also decrease the details of the model of the body in step 106 by replacing selected elementary spaces (6) with less elementary spaces (5) defined based on the signed distance and weight parameters of the selected elementary spaces (6). Again, the replacing does not imply that the original elementary spaces cease to exist, but that a hierarchically lower level elementary space was introduced in the model.

Figure 5:
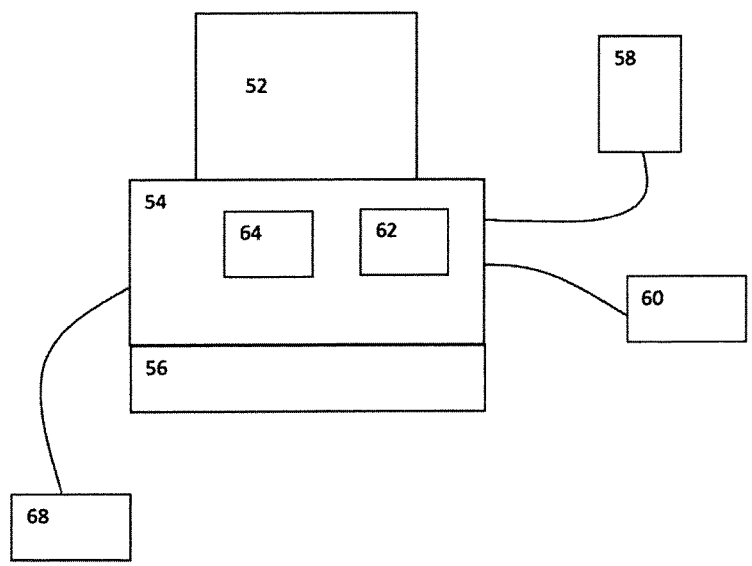
FIG. 5 shows a system in accordance with an embodiment of the present invention.
Figure 6:
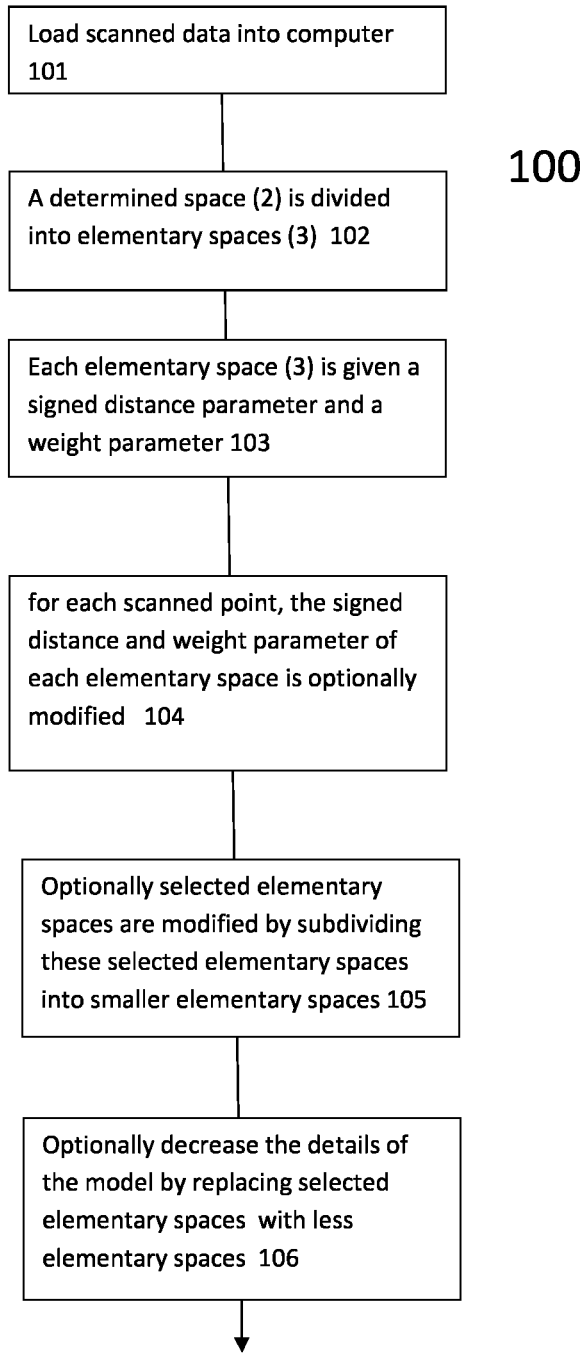
FIGS. 6 to 10 show flow diagrams for methods in accordance with embodiments of the present invention.
Figure 7:
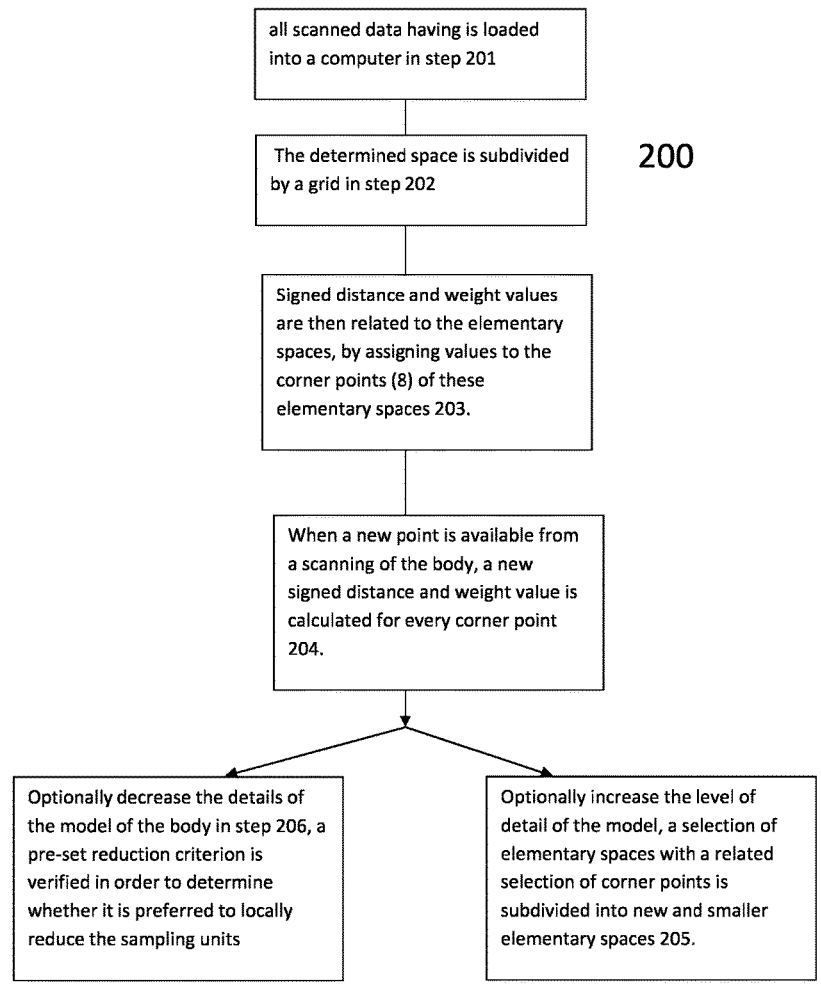

In a further particular way 200 of carrying out the method of the first aspect of the present invention is shown in FIG. 7, all scanned data having been loaded into a computer in step 201—such as computer 54 of FIG. 5. The determined space is subdivided by a grid (7) in step 202, as illustrated in FIGS. 1-*a* and *d* and 1-*c* and *f* for a two-dimensional case. The grid (7) divides the determined space in sampling units, e.g. regular sampling units, which define the elementary spaces. Preferably the grid coincides with the elementary spaces. Regular sampling units are equally sized sampling units. These equally sized sampling units are not necessarily cube shaped for example, because they could also be rectangular.

Signed distance and weight values are then related to the elementary spaces, for example by assigning values to the corner points (8) of these elementary spaces in step 203. Other specific points of said elementary spaces (e.g. midpoints of edges or faces, centre point of elementary space . . . ) can also be used for assigning distance and weight values, but are also referred to as corner points in the remainder of the text. When a new point is available from a scanning of the body, a new signed distance and weight value is calculated for every corner point in step 204. The current signed distance value of every corner point is then modified by replacing it with the weighted average of the new signed distance value and the current signed distance value, using the weight values as the weights for the average. The current weight value is then modified by replacing it with the sum of the current and new weight value. This means that when the calculated weight value is zero for a corner point, the new signed distance value will not be taken into account; hence there is no need to calculate a new signed distance value for this corner point.

Figure 3:
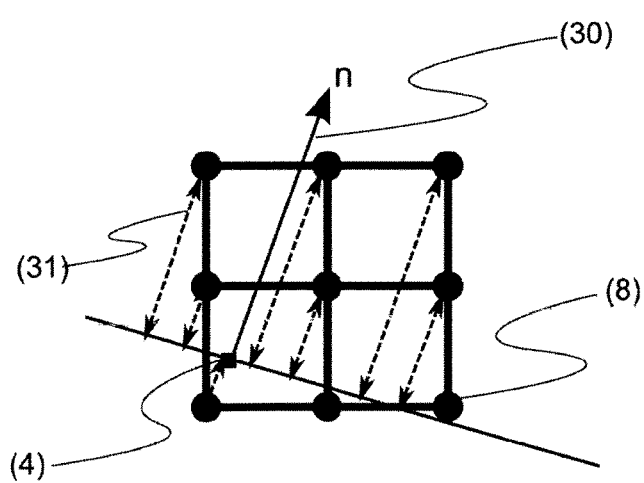
FIG. 3 shows an illustrative example of the calculation of signed distance values based on the scanned point and its normal.

A preferred way of calculating the new signed distance values is based on the scanned point and its normal (i.e. the direction perpendicular to the surface of the body in said point, which is typically estimated). First, a plane is fitted through the scanned point and perpendicular to the normal of that point. For each corner point, the distance is then measured between the corner point and this normal plane as illustrated in FIG. 3. The sign of the distance value is determined by whether the scanned point is inside (a minus sign) or outside (a plus sign) of the body. The information on the location inside or outside the body can be derived from the scanned points, but can also be specified by the scanner device as extra information within the scanned point.

A preferred way of calculating the new weight value of a corner point is assigning it a '1' when the scanned point will result in a modification of the signed distance value for this corner point and assigning it a '0' otherwise. In other words, the weight value of a corner point represents the number of scanned points that resulted in a signed distance value for this corner point.

Another preferred way of calculating the new weight value is by giving it a confidence value related to the accuracy of the measurement or any combination of these or the like, for example a value between zero and hundred.

Figure 2:
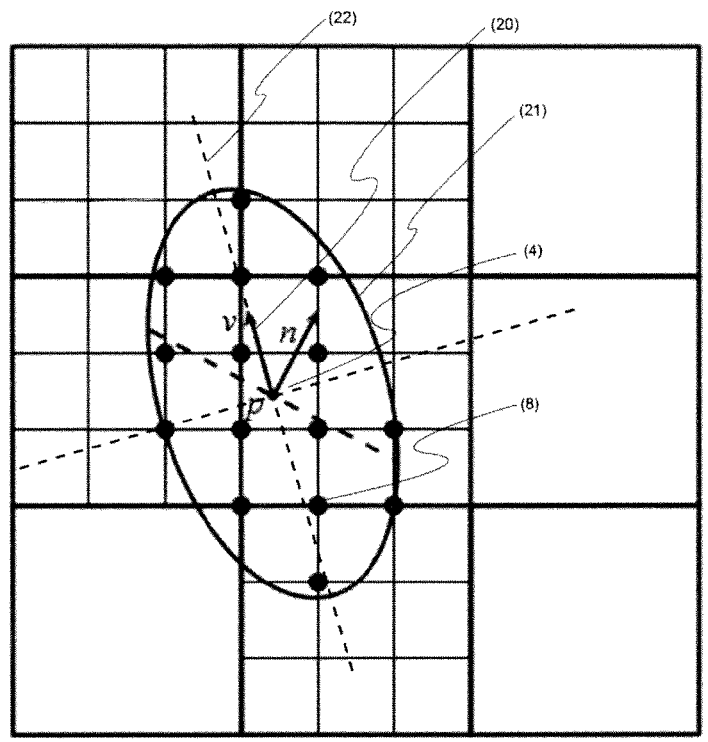
FIG. 2 shows an illustrative example of a neighbourhood comprising corner points according to a preferred embodiment of the invention.

Another preferred way of calculating the new weight value is determined by defining a neighbourhood around the scanned point in which the weight value is maximal at the scanned point itself and decreases to the border of the neighbourhood. The decrease can for instance be determined by a Gaussian function. Only the corner points lying within this neighbourhood are then updated with a new signed distance value and the respective weight value based on the position of the corner point within the neighbourhood itself as the new weight values outside the neighbourhood are assigned zero values. The size of this neighbourhood can depend on data provided by the scanner or by the scanned point density or the like. The neighbourhood can for example be defined by an ellipsoid (21) as illustrated in FIG. 2. The centre of this ellipsoid (21) is defined by the scanned point (4) and its long axis (22) aligned with the view direction of the scanner i.e. with the direction in which the scanned point was measured. The view direction can be specified by the scanner in the scanned point by means of a vector (20). A Gaussian function then defines the weight value within this ellipsoid; ranging from maximal in the scanned point (4) to the three sigma value on the border of the ellipsoid (21). Outside the ellipsoid the weight value is set to zero, so these corner points are not modified. For the corner points within this ellipsoid the said signed distance value and the respective weight value are determined in order to update the corner points. As such the uncertainty of the point location along the viewing direction and along the perpendicular direction is taken into account.

Alternatively, the weight value can be calculated by combining any or all of the previous ways to calculate the weight value.

In order to increase the level of detail of the model, a selection of elementary spaces (e.g. sampling units such as regular sampling units) with a related selection of corner points is subdivided into new and smaller elementary spaces (sampling units) in step 205. Regular sampling units are equally sized sampling units. These equally sized sampling units are not necessarily cube shaped for example, because they could also be rectangular. When subdividing an existing elementary space or lower-level elementary space into new elementary spaces or higher-level elementary spaces, corner points are generated at all the corners of the sampling unit itself and within that sampling unit. As these higher-level corner points are also corner points, they also need a signed distance and weight parameter to be assigned to. After creation of the higher-level corner point, its signed distance and weight parameters need to be initialized by assigning them an initial value. One preferred way to calculate the initial values is by giving them a default value, for example zero.

Another preferred way to calculate the initial value for the signed distance and weight parameters is by calculating the average of the neighbouring corner points that already existed before the subdivision, referred to as the neighbouring lower-level corner points.

Another preferred way to calculate the initial value for the signed distance and weight parameters is by using not only the values of the corner points of the sampling unit that is subdivided but also the values of the corner points of neighbouring sampling units (i.e. the same or higher or lower level corner points).

Another preferred way to calculate the initial value for the signed distance and weight parameters is calculate them based on the already acquired scanned points and optionally their metadata that are lying in a pre-defined neighbourhood (e.g. sphere, beam, ellipsoid . . . ) around this corner point. This means that the signed distance and weight values are calculated as if new acquired scanned points were added to the model calculating the values as described before. A preferred way to determine the neighbourhood size is by making it dependent of the sampling level. This means that the size of the neighbourhood and thus the area of influence is determined by the sampling level, i.e. the absolute size of the sampling unit, resulting in a different weight distribution for a scanned point depending on whether it is lying within an area with large or small sampling units. A typical example would be to reduce the influence area of a scanned point lying in a small sampling unit in order to mainly update higher level corner points.

Figure 4:
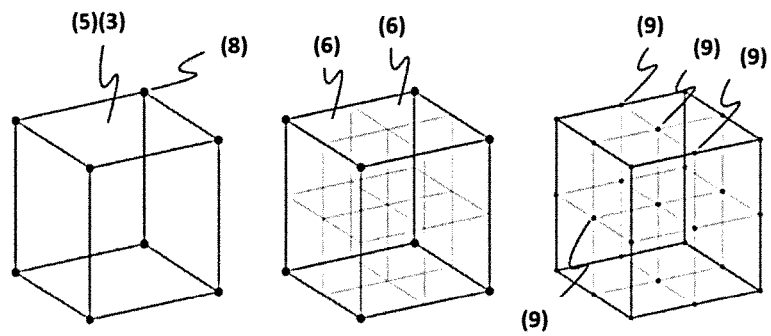
FIG. 4 shows an elementary space with its corner points (left), the higher-level elementary spaces through subdivision by means of an octree (middle) and the higher-level corner points (right).

A preferred way of subdividing the sampling units is by using an octree, where each sampling unit is subdivided in eight equally-sized units. The new corner points are then generated on all the corners of the sampling unit itself and on the centre of the sampling unit itself, its edges and its faces (FIG. 4). The calculation of the initial signed distance and weight values can then be done as described in the embodiment above. When doing the calculation based on a predefined neighbourhood the calculation is preferably done in the following way. For a new corner point that is in the same place as the lower-level corner point, the initial values are those of the existing corner point. For a new corner point in the middle of an edge, the initial values are the average of the values of the 2 lower level corner points at the end of the edge. For a new corner point added in the middle of a face the initial values are the average of the values of the 4 lower level corner points of the face, and for a new corner point added in the middle of the sampling unit the initial values are the average of the values of the 8 lower-level corner points of the lower-level sampling unit. This means that for the calculation of the weight and signed distance values to be assigned to the new higher-level corner points, trilinear interpolation of the 8 lower-level corner points is used.

At the moment new scanned points are added to already subdivided sampling units a preferred way is to modify only the higher-level corner points. Alternatively, all corner points or only the corner points of some level are updated.

The decision to subdivide the sampling units is preferably done by verifying a pre-set subdivision criterion for every sampling unit when a new scanned point is added to the model and thus new signed distance and weight values need to be calculated for the corner points. The pre-set criterion could comprise the point density to reduce the influence of noise on the 3D points and their metadata, but it could be any other criterion (e.g. confidence value of 3D points, surface curvature, any metadata or combinations of metadata or the like . . . ) or combination thereof.

One preferred subdivision criterion is a predefined minimal level of detail for the resulting surface representation. This means that whenever scanned points are added to a certain area of the determined space the sampling unit(s) is(are) first locally subdivided to the predefined size (i.e. for example the resolution or level of detail selected for the rough scanning approach) before calculating signed distance values and weight values for the respective corners points.

The subdivision process is not technically limited but can be limited by the implementation, for example the computation power or the memory needed to store all the corner points. Therefore, the pre-set criterion preferably limits the sampling units being subdivided to sampling units with dimensions smaller than the accuracy value of the measured scanned points.

In order to decrease the details of the model of the body in step 206, instead of the pre-set subdivision criterion, a pre-set reduction criterion can also be verified in order to determine whether it is preferred to locally reduce the sampling units, i.e. removing a subdivision of a sampling unit, and as a consequence decrease the level of detail of the future surface/volume representation. When using the preferred octree, the reduction is done by removing the 8 equally-sized units and returning back to the previous sampling unit (i.e. the lower level) comprising these 8 units. Within the octree this can be done by removing all the children nodes of the lower level sampling unit. This means that the data stored in the corners of the 8 units (i.e. in the higher level corner points) is removed and the corner points of the lower level sampling unit are updated. When removing the higher level corner points, the signed distance and weight values of the corresponding lower level corner points are updated. This is preferably done by just keeping existing signed distance and weight values of the lower level corner point; hence no update is done. Alternatively the signed distance and weight value of the lower level corner point are replaced by the values of the corresponding higher level corner point that is removed. Alternatively the signed distance value and the weight value of the lower level corner points are replaced by a combination of the values of the low and high level corresponding corner points. Alternatively, the signed distance value and the weight value of the lower level corner points are replaced by a certain combination of the values for the low and high level corresponding corner points and of the values of some or all of the neighbouring higher level corner points. Alternatively, the signed distance value and the weight value of the lower level corner points are calculated based on the values of the higher level corner points of the sampling units that are removed and the values of corner points of neighbouring sampling units (level can be the same, higher or lower). Alternatively, the signed distance value and the weight value of the lower level corner points are calculated based on the initial scanned points that are lying in a pre-defined neighbourhood (e.g. sphere, beam, ellipsoid . . . ) around the corner point.

The said pre-set reduction criterion should define the minimal detail, which can be based for instance on the needed detail to describe the surface/volume accurately. For example a smooth surface can be accurately represented by a surface with a low level of detail while a highly curved surface needs a higher level of detail for an accurate representation. The reduction criterion could be a maximal value for the curvature (e.g. Gaussian curvature, mean curvature . . . ), a maximal change in surface normal, a maximal distance error relative to the high-detail surface representation or the like. Alternatively, external input, for example from a user, can be used to indicate the areas where low level of detail is allowed.

The pre-set criteria for increasing or reducing the level of detail can be set in an adaptive manner, meaning that once these are met for a certain sampling unit these are adapted. This would mean that for the corner points not only the signed distance value and the weight value are stored but also the values for the criteria. This way of working will avoid that sampling units are very often subdivided and reduced.

The steps of modifying the corner point, increasing the detail and decreasing the detail can be iteratively repeated as new scanned points are obtained. It is thereby not required that all steps are performed with every scanned point. For example, one can modify the corner points with new scanned points without verifying the pre-set criterion and thus without deleting or adding corner points and only verify the criterion after a certain amount of scanned points.

At any point in time, the corner points with their signed distance and weight values comprise a model of the body that is scanned taking into account the already scanned points. At any point in time, this model can be used to derive a surface or volume representation of the body. A typical example of a surface representation is a triangular mesh. Such a mesh can be obtained from the model of the body by state-of-the-art meshing techniques, like the Marching Cubes or the Marching Tetrahedra algorithm: see for example Lorensen, W. E.; Cline, Harvey E. (1987). "Marching cubes: A high resolution 3d surface construction algorithm". *ACM Computer Graphics vol.* 21 (4) pages 163-169 and for example Akio Doi and Akoi Koide, "An efficient method of triangulating equi-valued surfaces by using tetrahedral cells", IEICE Trans Commun. Elec. Inf. Syst, E-74(1) pages 213-224, 1991.

Therefore meshing is done by extracting the 0-isosurface (i.e. the surface that goes through the points where distance equals 0) in the sampling units. For the evaluation of the signed distances there are different options, either all signed distance values (i.e. at all levels of subdivision) are used or only the highest level values are used, or any combination of different levels. A typical way to visualize volumetric data is volume rendering. This is done by state-of-the-art techniques, like the volume ray casting algorithm, which is based on the principle of shooting rays from the eye through each pixel of the image and finding the closest object blocking the path of that ray. The signed distance and weight values are used to determine the intersection between the ray and the volume and to determine the color of the corresponding pixel.

Alternatively the weight values are used either during the evaluation to decide whether or not a surface or volume representation needs to be created or during the visualization of the surface or volume to decide whether or not to hide certain parts.

Embodiment According to the Second Aspect of the Invention

Figure 8:
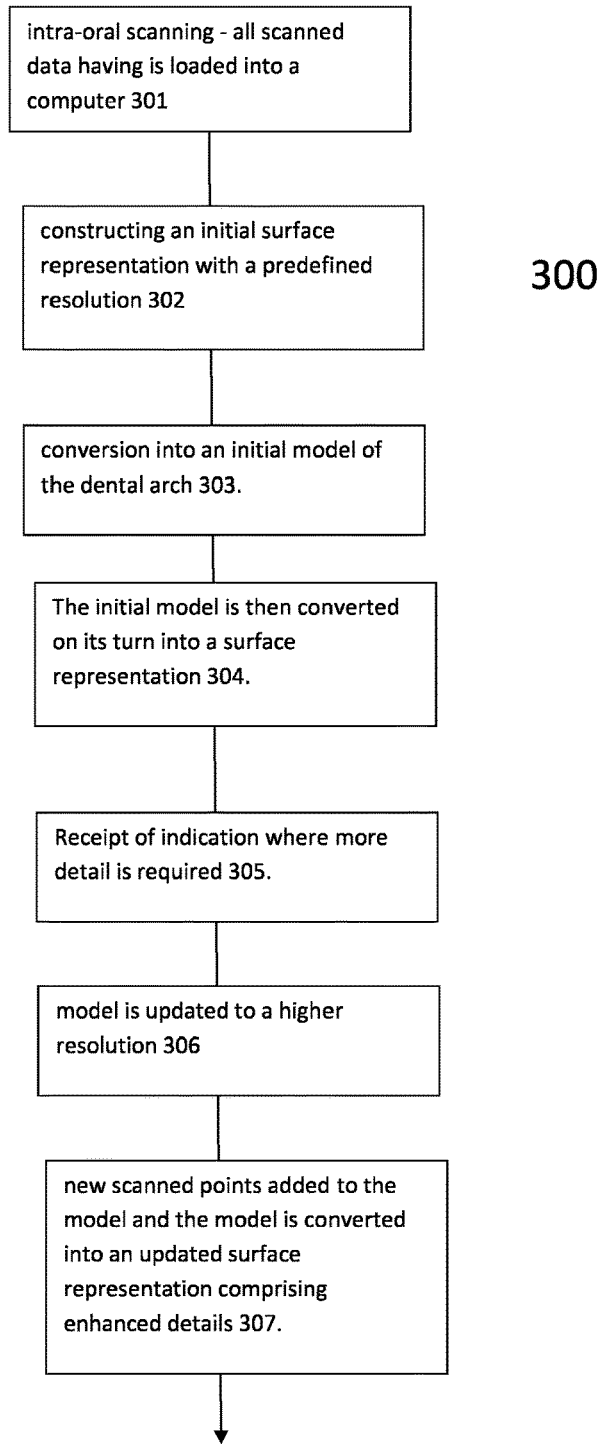

In a preferred embodiment of the second aspect of the present invention the method from the first aspect of the present invention is used in a method 300 for obtaining a 3D digital surface representation of a dental arch. Initial measurement data and thus scanned points are then acquired via an intra-oral scanner. All scanned data is loaded into a computer in step 302—such as computer 54 of FIG. 5. An initial surface representation is constructed with a predefined resolution in step 302 of FIG. 8. The predefined resolution is specified by the subdivision criterion in the disclosed method. These initial scanned points are then converted into an initial model of the dental arch by applying the method of the first aspect of the invention in step 303. The initial model is then converted on its turn into a surface representation in step 304. The surface is converted into an image and displayed to the user, i.e. the dentist. The user then indicates on this display where more detail is required in step 305. This user input is then translated into a starting point for the scanner for the acquisition of a new set of data and the pre-set criterion in this location of the model is updated to a higher resolution in step 306. The pre-set criterion could also stay unchanged, if it is for example specified so that the detail is increased based on the number of scanned points in this location. The new scanned points are then added to the model and the model is converted into an updated surface representation comprising enhanced details in the selected areas in step 307.

In a preferred embodiment of the second aspect of the present invention the method from the first aspect of the present invention is used for obtaining a further 3D digital surface representation of a dental arch in multiple scan sessions. Initial measurement data and thus scanned points are acquired via an intra-oral scanner such as an intra-oral optical scanner constructing an initial surface representation with a predefined resolution of part of the dental arch. The predefined resolution is specified by the subdivision criterion in the disclosed method. These initial scanned points are then converted into an initial model of part of the dental arch by applying the method of the first aspect of the invention. The initial model is then converted on its turn into a surface representation which is converted into an image and displayed to the user, i.e. the dentist. In a next scan session the user then indicates on this display where the scan needs to be extended. This user input is then translated into a starting point for the scanner for the acquisition of a new set of data. The new scanned points are then added to the model and the model is converted into an updated surface representation comprising the additionally scanned part of the dental arch.

In a further embodiment of the second aspect of the present invention the user can indicate on the display that a part of the surface representation needs to be invalidated. For the elements within the indicated area the weight values are set to zero and the surface representation is updated by hiding the surface in the area with weight value zero. Optionally sampling units can be reduced as well. When continuing the scanning operation the method of the first aspect of the invention is used to add new scanned points.

When the user is responsible for the scanning device, i.e. for deciding if and where additional scanned points are obtained, the image of the surface representation can be used to indicate where the pre-set criterion is not met, i.e. where more scanned points are desired. The user can then scan extra scanned points in that area until the criterion is met. Once the level of detail is as desired or specified the visual feedback can be adapted to inform the user that additional scanning is no longer needed in that area.

Figure 9:
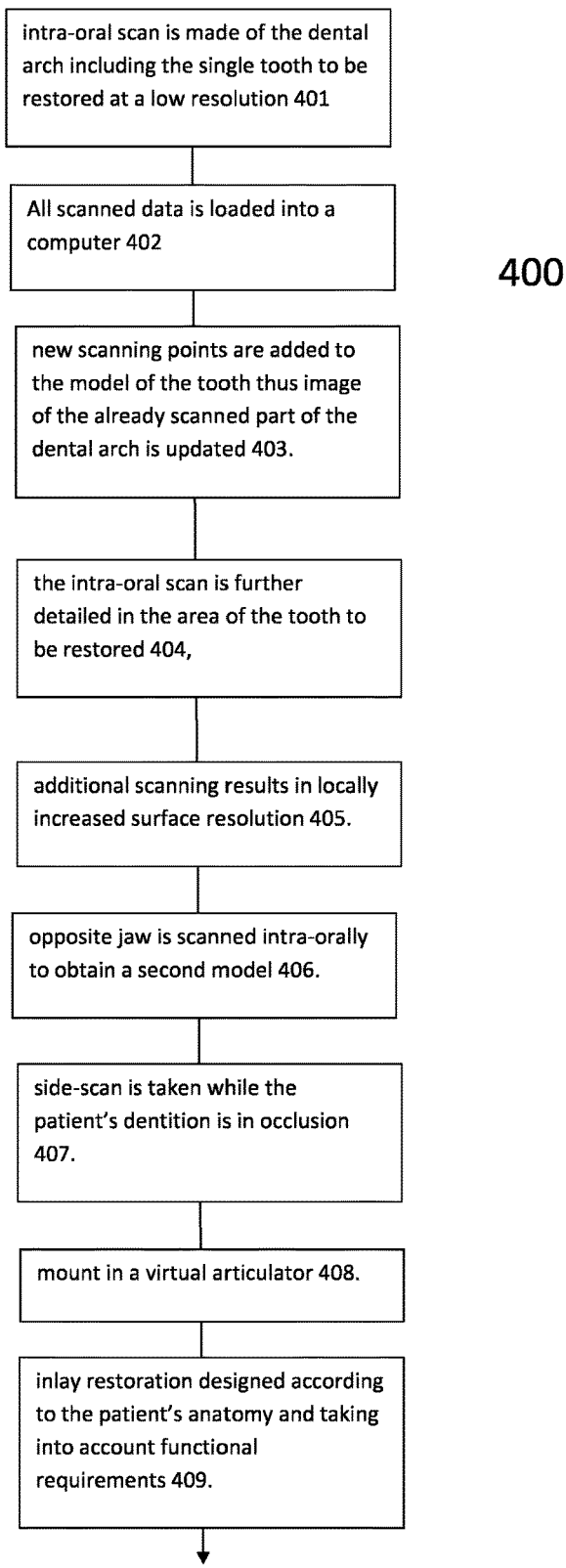

According to another embodiment of the second aspect of the invention which is to be understood as an implementation of the methods described above, the dentition for the treatment of a single tooth with an inlay restoration is digitized in a method 400 as shown in FIG. 9. At first an intra-oral scan is made of the dental arch including the single tooth to be restored at a low resolution in step 401. Thus the intra-oral scanning device is moved along the dental arch. All scanned data is loaded into a computer in step 402—such as computer 54 of FIG. 5. In the meantime, the new scanning points are added to the model of the tooth and at regular intervals the surface representation and thus image of the already scanned part of the dental arch is updated in step 403. As such the user gets visual feedback on the progress of the scanning and can easily verify when the scan is complete. For the tooth to be restored, a highly detailed model is needed in order to be able to design and manufacture a well-fitting inlay restoration. Therefore, the intra-oral scan is further detailed in the area of the tooth to be restored in step 404, by scanning additional scanned points in this area. The additional scanning will result in locally increased surface resolution in step 405. While scanning, the user could be given visual feedback regarding the level of detail of the surface representation by means of a code of which a colour code is only one option. As such the user can easily decide to stop the scanning at the moment the area of interest, i.e. the tooth to be restored and optionally its neighbouring teeth, is sufficiently detailed. In a next step the opposite jaw is scanned intra-orally to obtain a second model in step 406. Then a side-scan is taken while the patient's dentition is in occlusion in step 407. By means of the side scan the 3D digital models of both dental arches are put virtually in occlusion (i.e. by using dedicated registration algorithms or the like see for example Chen, Yang; Gerard Medioni (1991). "Object modelling by registration of multiple range images". *Image Vision Comput.* (Newton, Mass., USA: Butterworth-Heinemann) pages 145-155 and are mounted in a virtual articulator (see for example WO2009133131 (A1) incorporated herein by reference) in step 408. Based on the occlusion and articulation simulation the inlay restoration can be designed according to the patient's anatomy and take into account functional requirements in step 409.

Figure 10:
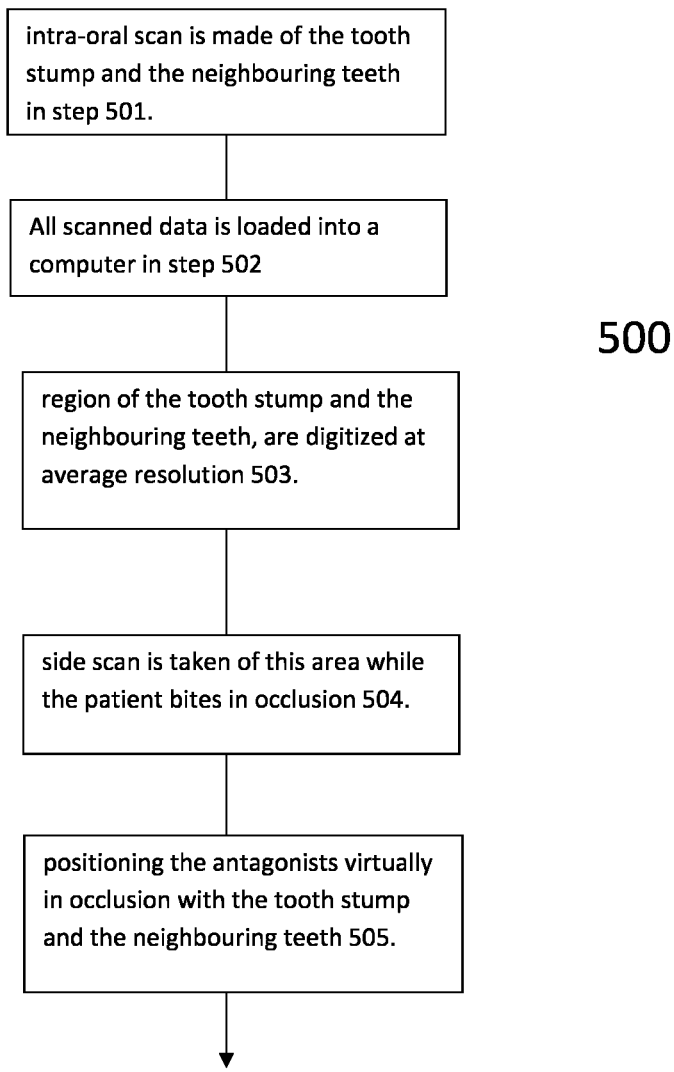

According to another embodiment of the second aspect of the invention, a tooth stump and its marginal edge as well as the neighbouring teeth and the antagonists are digitized in order to design a crown restoration in a method 500 as shown in FIG. 10. At first an intra-oral scan is made of the tooth stump and the neighbouring teeth in step 501. All scanned data is loaded into a computer in step 502—such as computer 54 of FIG. 5. Thereto the scanner is moved along the teeth and the tooth stump in order to obtain a high resolution model of these. Especially at the marginal edge of the tooth stump a highly detailed surface representation is needed in order to be able to detect this marginal edge with high accuracy, needed to design a well-fitting crown. Secondly the antagonists, i.e. for the region of the tooth stump and the neighbouring teeth, are digitized at average resolution in step 503. Also a side scan is taken of this area while the patient bites in occlusion in step 504. The side scan is used for positioning the antagonists virtually in occlusion with the tooth stump and the neighbouring teeth in step 505. As such it is possible to shape the surface of the occlusion of the crown so that it occludes well with the antagonists.

According to a preferred embodiment of the invention the volumetric construction by means of multi-resolution sampling units can be performed as a parallel process, which refers to executing/running the dedicated algorithms in parallel, i.e. at the same time on multiple processors or any device suited for performing these calculations. Well-known examples of parallel processes are multi-threading and CUDA, but parallel processing is within the scope of this invention not limited to these.

According to another embodiment of the second aspect of the invention, a watertight model is created. A watertight model is defined as a model without holes or non-manifold edges, and without geometric overlaps or intersections in the model, and without geometric errors producing unrealistically thin areas. A typical state-of-the-art algorithm for creating watertight models is the Poisson surface reconstruction which uses a point cloud as input. This Poisson reconstruction algorithm exists of 3 steps, (1) converting the points into a specific data structure, (2) fitting a function through the data generated in step 1, and (3) generating the watertight surface representation. The Poisson surface reconstruction algorithm has been modified in order to be able to directly use the representation of the body to be digitized by means of elementary spaces and distance and weight parameters as input. So only the second and third steps need to be applied. The second step, fitting a function onto the distance values of the elementary spaces generates distance values in elementary spaces where no scanned points were added (and thus no distance values were yet available) and approximates the distance values in the other elementary spaces as good as possible. The third step, generating the watertight model, is done by evaluation the function in all elementary spaces (even those where no scanned points were added) and generating an iso-surface. This approach has the advantage that a watertight model is generated faster since the first step (i.e. converting the points into a specific data structure) of the typical Poisson reconstruction algorithm is no longer needed.

FIG. 5 shows schematically a system 50 in accordance with embodiments of the present invention. All methods according to embodiments of the present invention and systems according to the present invention can be implemented on computer system 50 that is specially adapted to implement methods of the present invention. The computer system 50 includes a computer 54 with a processor 62 and memory 64 and preferably a display 52. Any of the methods of the present invention can be based on the computer 54 having means for generating and visualizing a 3D model. Each such a method can be implemented on the computer 54 by providing software that when run on the computer. An input device such as a scanner 58 or signal storage station 60 is provided for inputting data for the 3D model, e.g. the signal storage device 60 may be a storage device such as a CD-ROM, or solid state memory or a storage means via a network link, e.g. via a LAN or WAN.

The computer 54 can comprise a processor 62 and a memory 64, which stores machine-readable instructions (software as described above) which, when executed by the processor 54 cause the processor to perform the described methods. A computing system which can be utilized with the methods of the present invention may run computer programs such as 3-Matic™ as supplied by Materialise N.V., Leuven, Belgium. The computer may include a video display terminal 52, a data input means such as a keyboard, 56 and a graphic user interface indicating means such as a mouse 68. The computer may be implemented as a general purpose computer, e.g. a UNIX workstation or a personal computer or a laptop.

The computer 54 typically includes a Central Processing Unit ("CPU"), such as a conventional microprocessor of which a Pentium processor supplied by Intel Corp. USA is only an example, and a number of other units interconnected via bus system. The bus system may be any suitable bus system. The computer includes at least one memory. Memory may include any of a variety of data storage devices known to the skilled person such as random-access memory ("RAM"), read-only memory ("ROM"), and non-volatile read/write memory such as a hard disc as known to the skilled person. For example, the computer may further include random-access memory ("RAM"), read-only memory ("ROM"), as well as a display adapter for connecting the system bus to a video display terminal, and an optional input/output (I/O) adapter for connecting peripheral devices (e.g., disk and tape drives) to the system bus. The video display terminal can be the visual output of computer, and can be any suitable display device such as a CRT-based video display well-known in the art of computer hardware. However, with a desk-top computer, a portable or a notebook-based computer, the video display terminal can be replaced with a LCD-based or a gas plasma-based flat panel display. The computer further includes an user interface adapter for connecting a keyboard, mouse, and optional speaker.

The computer can also include a graphical user interface that resides within machine-readable media to direct the operation of the computer. Any suitable machine-readable media may retain the graphical user interface, such as a random access memory (RAM), a read-only memory (ROM), a magnetic diskette, magnetic tape, or optical disk (the last three being located in disk and tape drives). Any suitable operating system and associated graphical user interface (e.g., Microsoft Windows, Linux) may direct CPU. In addition, computer includes a control program that resides within computer memory storage. Control program contains instructions that when executed on CPU allow the computer to carry out the operations described with respect to any of the methods of the present invention.

The graphical user interface is used to visualize the 3D model. Those skilled in the art will appreciate that other peripheral devices such as optical disk media, audio adapters, or chip programming devices, such as PAL or EPROM programming devices well-known in the art of computer hardware, and the like may be utilized in addition to or in place of the hardware already described.

The computer program product for carrying out the method of the present invention can reside in any suitable memory and the present invention applies equally regardless of the particular type of signal bearing media used to actually store the computer program product. Examples of computer readable signal bearing media include: recordable type media such as floppy disks and CD ROMs, solid state memories, tape storage devices, magnetic disks.

Accordingly, the present invention also includes a software product which when executed on a suitable computing device carries out any of the methods of the present invention. Suitable software can be obtained by programming in a suitable high level language such as C and compiling on a suitable compiler for the target computer processor. Such methods will now be described. The present invention provides a computer program product in the form of software. The software is adapted such that when it is executed on a suitable processing engine, a body can be modelled from scan data of a determined space. The scanning of said body provides scanned points. These are divided into elementary spaces, each elementary space being assigned a signed distance parameter indicative of the distance of said elementary space to said body, and a weight parameter indicative of the importance of the distance parameter.

The software can be adapted such that when it is executed on a suitable processing engine, each scanned point thus obtained optionally modifies said signed distance and weight parameters of each elementary space of said determined space.

The software can be adapted such that when it is executed on a suitable processing engine details of the model of said body can be increased by each one of selected elementary spaces of said determined space being modified by subdividing said selected elementary space into higher level elementary spaces (defined by the same parameters as said selected elementary spaces.

The software is adapted such that when it is executed on a suitable processing engine, details of the model of said body can be decreased by said elementary spaces of said determined space being modified by replacing selected elementary spaces with lower level elementary spaces defined by the same parameters as said selected elementary spaces.

The software can be adapted such that when it is executed on a suitable processing engine said modifying of said signed distance and weight parameter is performed by calculating a new signed distance and weight value based on said scanned point; and replacing the current value of said signed distance parameter with an updated signed distance value based on said new signed distance and weight value and on said current value of said signed distance parameter and on the current value of said weight parameter; and replacing said current value of said weight parameter with an updated weight value based on said current value of said weight value and said new weight value.

The software can be adapted such that when it is executed on a suitable processing engine said updated signed distance value is the weighted average between said new distance value and said current value of said signed distance parameter; said weighted average using said new weight value and said current weight value of said signed distance parameter as weights for said new weight value and said current weight value respectively.

The software can be adapted such that when it is executed on a suitable processing engine said new signed distance value is the distance between a normal plane fitted through said scanned point and said elementary space; and wherein the sign of said new signed distance value is positive if said elementary space is located outside of said body and wherein the sign of said value is negative if said elementary space is located inside of said body.

The software can be adapted such that when it is executed on a suitable processing engine said updated weight value is the sum of said current value of said weight parameter and said new weight value.

The software can be adapted such that when it is executed on a suitable processing engine said new weight parameter is calculated by determining a neighbourhood, comprising borders and a centre around the scanned point, in which the value of said weight parameter is maximal in the elementary space containing said scanned point; and said value is decreasing towards the borders of said neighbourhood; and said value is zero outside the border of said neighbourhood.

The software can be adapted such that when it is executed on a suitable processing engine said scanned point contains information on the viewing direction of said scanning and said neighbourhood is an ellipsoid. The scanned point is preferably at the centre of said ellipsoid. The long axis of said ellipsoid can be defined by the viewing axis of the scanner. Said new weight value can be determined by a Gaussian function within said ellipsoid. Said Gaussian function can range from a maximum in the centre of the ellipsoid to the three sigma value on the border of the ellipsoid.

The software can be adapted such that when it is executed on a suitable processing engine said elementary spaces are defined by a grid subdividing said determined space in sampling units such as regular sampling units, each said sampling unit, such as regular sampling unit corresponding to a single elementary space. Regular sampling units are equally sized sampling units. These equally sized sampling units are not necessarily cube shaped for example, because they could also be rectangular.

In a preferred embodiment the software can be adapted such that when it is executed on a suitable processing engine said sampling units are represented by the nodes of a tree such as an octree and said subdividing of said selected elementary spaces is performed by dividing each said sampling unit in a number such as eight child sampling units. The software can be adapted such that when it is executed on a suitable processing engine said reducing each one of said elements to hierarchically higher level elements is performed by removing all the child nodes of the node corresponding to said element.

In a less preferred embodiment the software can be adapted such that when it is executed on a suitable processing engine said corner points are represented by the nodes of an octree and said subdividing of said selected elementary spaces and thus selected corner points is performed by equally dividing each said regular sampling unit corresponding to said selected corner point in a number such as a number such as eight sampling units such as eight identically sized regular sampling units each corresponding to a number such as eight new corner points, each said new corner point represented as a new child node of the node representing said selected corner point. The software can be adapted such that when it is executed on a suitable processing engine said reducing each one of said elements to hierarchically higher level elements and thus reducing each one of said corner point to a higher level corner point is performed by removing all the child nodes of the node corresponding to said corner point.

The software for any embodiment of the present invention can be adapted such that when it is executed on a suitable processing engine the signed distance and weight parameters are assigned to the corner points of said elementary space.

The software can be adapted such that when it is executed on a suitable processing engine said selected elementary spaces for subdividing are defined by a pre-set subdivision criterion and said selected elementary spaces for replacing are defined by a pre-set reduction criterion.

The software can be adapted such that when it is executed on a suitable processing engine a digital surface or volume representation is constructed from said distance and weight parameters of said elementary spaces.

The software can be adapted such that when it is executed on a suitable processing engine said surface or volume representation is constructed by extracting the 0-isosurface.

The software can be adapted such that when it is executed on a suitable processing engine said preset subdivision criterion is the minimal level of detail needed in said surface or volume representation.

The invention claimed is:

1. A method comprising the steps of:
   modelling a body from a scanning of a determined space, a digital volume or a surface representation being obtainable from the modelling at any time during the scanning process;
   dividing the determined space into elementary spaces, each elementary space being assigned
   a signed distance parameter indicative of the distance of said elementary space to said body,
   a weight parameter indicative of the importance of the distance parameter;
   said scanning of said body providing scanned points;
   wherein, in order to increase details of the model of said body, each one of selected elementary spaces of said determined space are modified by subdividing said selected elementary space into higher level elementary spaces defined by the same parameters as said selected elementary spaces;
   wherein, in order to decrease details of the model of said body, said elementary spaces of said determined space are modified by replacing selected elementary spaces with lower level elementary spaces defined by the signed distance and weight parameters of said selected elementary spaces, the increasing of the detail of the model and the decreasing of the detail of the model being iteratively repeated as new scanned points are obtained, and
   rendering the digital volume or surface representation to obtain an image of the scanned object on a display at any time during the scanning process.

2. A computer based system for modelling a body by scanning a determined space of the body, digital volume or a surface representation being obtainable from the modelling at any time during the scanning process, the system comprising a computer with a processor and said scanning of said body providing scanned points, the processor being adapted to divide the determined space into elementary spaces, the processor being adapted to assign for each elementary space:
   a signed distance parameter indicative of the distance of said elementary space to said body,
   a weight parameter indicative of the importance of the distance parameter;
   wherein, in order to increase details of the model of said body, the processor is adapted to modify each one of selected elementary spaces of said determined space by subdividing said selected elementary space into higher level elementary spaces defined by the same parameters as said selected elementary spaces;
   wherein, in order to decrease details of the model of said body, the processor is adapted to modify said elementary spaces of said determined space by replacing selected elementary spaces with lower level elementary spaces defined by the signed distance and weight parameters of said selected elementary spaces, wherein the increasing of the detail of the model and the decreasing of the detail of the model are iteratively repeated as new scanned points are obtained, and
   the processor is adapted to render the digital volume or surface representation to obtain an image of the scanned object on a display at any time during the scanning process.

3. The computer based system according to claim 2 said processor being further adapted to modify said signed distance and weight parameter by calculating a new signed distance and weight value based on said scanned point; and replacing the current value of said signed distance parameter with an updated signed distance value based on said new signed distance and weight value and on said current value of said signed distance parameter and on the current value of said weight parameter; and replacing said current value of said weight parameter with an updated weight value based on said current value of said weight value and said new weight value.

4. The computer based system according to claim 3 wherein the processor is further adapted so that said updated signed distance value is the weighted average between said new distance value and said current value of said signed distance parameter; said weighted average using said new weight value and said current weight value of said signed distance parameter as weights for said new weight value and said current weight value respectively.

5. The computer based system according to claim 3 wherein the processor is further adapted so that said new signed distance value is the distance between a normal plane fitted through said scanned point and said elementary space; and wherein the sign of said new signed distance value is positive if said elementary space is located outside of said body and wherein the sign of said value is negative if said elementary space is located inside of said body.

6. The computer based system according to claim 2 wherein the processor is further adapted so that said updated weight value is the sum of said current value of said weight parameter and said new weight value.

7. The computer based system according to claim 2 wherein the processor is further adapted so that said new weight parameter is calculated by determining a neighbourhood, comprising borders and a centre around the scanned point, in which the value of said weight parameter is maximal in the elementary space containing said scanned point; and said value is decreasing towards the borders of said neighbourhood; and said value is zero outside the border of said neighbourhood.

8. The computer based system according to claim 7 wherein the processor is further adapted so that said scanned point contains information on the viewing direction of said scanning; and wherein said neighbourhood is an ellipsoid wherein said scanned point is the centre of said ellipsoid; and wherein the long axis of said ellipsoid is defined by the viewing axis of the scanner and wherein said new weight value is determined by a Gaussian function within said ellipsoid; said Gaussian function ranging from a maximum in the centre of the ellipsoid to the three sigma value on the border of the ellipsoid.

9. The computer based system according to claim 8 wherein the processor is further adapted so that said sampling units are represented by the nodes of a tree; and wherein said subdividing said selected elementary spaces is performed by dividing each said sampling unit in child sampling units, or equally sized sampling units; and wherein said reducing said selected elementary spaces is performed by removing all child sampling units of said sampling unit.

10. The computer based system according to claim 2 wherein the processor is further adapted so that said elementary spaces are defined by a grid subdividing said determined space in regular sampling units, each said regular sampling unit corresponding to a single elementary space.

11. The computer based system according to claim 10 wherein the processor is further adapted so that the signed distance and weight parameters are assigned to corner points of said elementary space.

12. A computer based system of claim 11, wherein the corner points are modified for new scanned points by deleting or adding corner points only after receipt of an amount of scanned points.

13. A computer based system of claim 12, wherein the corner points are selected from midpoints of edges or faces or centre points of elementary spaces.

14. The computer based system according to claim 2 wherein the processor is further adapted so that said selected elementary spaces for subdividing are defined by a pre-set subdivision criterion and wherein said selected elementary spaces for replacing are defined by a pre-set reduction criterion.

15. The computer based system according to claim 14 wherein the processor is further adapted so that said preset subdivision criterion is the minimal level of detail needed in said surface or volume representation.

16. A computer based system for modelling a body according to claim 14, wherein said pre-set reduction criterion defines the minimal detail needed to describe the surface representation accurately.

17. A computer based system for modelling a body according to claim 16 wherein said pre-set reduction criterion is a maximal value of curvature, a maximal change in surface normal, or a maximal distance error relative to a high-detail surface representation.

18. The computer based system according to claim 2 wherein the processor is further adapted so that a digital surface or volume representation is constructed from said distance and weight parameters of said elementary spaces.

19. The computer based system according to claim 18 wherein the processor is further adapted so that said surface or volume representation is constructed by extracting the 0-isosurface.

20. The computer based system according to claim 19 wherein the processor is further adapted so that said preset subdivision criterion is the minimal level of detail needed in said surface or volume representation.

21. The computer based system according to claim 18 wherein the processor is further adapted so that said preset subdivision criterion is the minimal level of detail needed in said surface or volume representation.

22. A computer based system of claim 2, the processor being further adapted to modify said signed distance and weight parameters of each elementary space of said determined space on receipt of each new scanned point obtained by the scanning.

23. A non-transient computer program product stored on a signal storage medium, the computer program product comprising software which when executed on a processing engine is for modelling a body from a scanning of a determined space of the body, said scanning of said body providing scanned points, digital volume or a surface representation being obtainable from the modelling at any time during the scanning process, the computer program product comprising code segments for dividing the determined space into elementary spaces, to assign for each elementary space:
  a signed distance parameter indicative of the distance of said elementary space to said body,
  a weight parameter indicative of the importance of the distance parameter;
  wherein, in order to increase details of the model of said body, the software is adapted to modify each one of selected elementary spaces of said determined space by subdividing said selected elementary space into higher level elementary spaces defined by the same parameters as said selected elementary spaces;
  wherein, in order to decrease details of the model of said body, the software is adapted to modify said elementary spaces of said determined space by replacing selected elementary spaces with lower level elementary spaces defined based on the signed distance and weight parameters of said selected elementary spaces, the increasing of the detail of the model and the decreasing of the detail of the model being iteratively repeated as new scanned points are obtained.

* * * * *